United States Patent [19]

Umezawa et al.

[11] 4,255,564
[45] Mar. 10, 1981

[54] NOVEL MACROLACTONE DERIVATIVES AND PROCESS OF PRODUCING THEM

[75] Inventors: Sumio Umezawa; Hamao Umezawa; Kuniaki Tatsuta, all of Tokyo, Japan

[73] Assignee: Zaidan Hojin Biseibutsu Kagaku Kenkyu Kai, Tokyo, Japan

[21] Appl. No.: 75,036

[22] Filed: Sep. 12, 1979

Related U.S. Application Data

[62] Division of Ser. No. 883,301, Mar. 3, 1978, Pat. No. 4,196,280.

[30] Foreign Application Priority Data

Mar. 9, 1977 [JP] Japan .................................. 52/25618
Mar. 9, 1977 [JP] Japan .................................. 52/25619
May 12, 1977 [JP] Japan .................................. 52/55125

[51] Int. Cl.³ .................... C07H 17/08; C07D 313/00
[52] U.S. Cl. ...................................... 536/17 R; 536/9; 260/343.41
[58] Field of Search .......................... 536/9, 17 R, 17; 260/343.41

[56] References Cited

U.S. PATENT DOCUMENTS 3,923,784  12/1975  Kierstead et al. ...................... 536/9
3,928,387  12/1975  Kierstead et al. ...................... 536/9

OTHER PUBLICATIONS

Omura, S., et al., J. Antibiotics, 27(2) 1974(147-149).

Primary Examiner—Johnnie R. Brown
Assistant Examiner—Blondel Hazel
Attorney, Agent, or Firm—Burgess, Ryan and Wayne

[57] ABSTRACT

By protecting the aldehyde group of a macrolide series antibiotics with a cyclic acetal or thioacetal, novel macrolide derivatives can be produced from the macrolide series antibiotics by releasing successively, the sugar moieties bonded to the macrolide antibiotics.

The novel marcolide derivatives obtained by this invention, that is, the derivatives of a macrolide series antibiotics produced by releasing partially or wholly the sugar moieties bonded are useful as intermediates for producing novel macrolide series antibiotics.

21 Claims, No Drawings

NOVEL MACROLACTONE DERIVATIVES AND PROCESS OF PRODUCING THEM

This is a continuation of application Ser. No. 883,301, filed Mar. 3, 1978 now U.S. Pat. No. 4,196,280.

BACKGGROUND OF THE INVENTION

1. Field of the Invention

The present invention relates to novel macrolactone derivatives useful as intermediates for producing novel macrolide series antibiotics and also to a novel process of producing the macrolactone derivatives by releasing sugar moieties from macrolide series antibiotics.

2. Description of the Prior Art

Macrolide series antibiotics which are widely used for the treatment of diseases caused by the infection of various microorganisms, are composed of an aglycone moiety and sugar moieties. It has been attempted to improve the antimicrobial spectrum, the antimicrobial activity, and the therapeutic effect of the macrolide series antibiotics by converting the sugar moiety thereof into another sugar moiety of other macrolide series antibiotics or derivatives thereof, or into other sugar residues that have not yet been known in macrolide series antibiotics or derivatives thereof, or further into other substituent than sugars. However, when the aldehyde group and the hydroxyl group residue in a sterically close site with each other on the aglycone of a macrolide series antibiotics, acetal is formed in the molecule of the aglycone to stabilize it after the elimination of sugar moiety and causes difficulties to introduce thereto a desired new sugar moiety or other substituents. Therefore, it has been desired to develop a process capable of releasing a part or the whole of sugar moieties from macrolide series antibiotics to provide intermediates which are useful for the production of novel macrolide series antibiotics by introducing new sugar moieties or substituents.

SUMMARY OF THE INVENTION

As the result of various investigations to overcome the aforesaid problem, the inventors have discovered derivatives of the aglycones of macrolide series antibiotics to which new sugars or substituents can be very easily introduced without forming intramolecular acetal.

For example, according to this invention, there is provided the aglycone of a macrolide compound represented by the general formula (1)

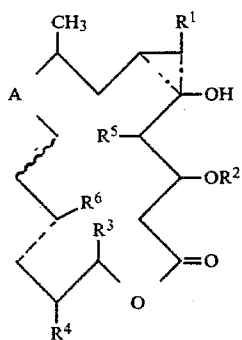

wherein A represents a carbonyl group or RO —< group; R represents a hydrogen atom, an acyl group, or a forosaminyl group; $R^1$ represents an aldehyde group protected by a cyclic acetal or thioacetal; $R^2$ represents a hydrogen atom or an acyl group; $R^3$ represents a lower alkyl group; $R^4$ represents a hydrogen atom, a hydroxymethyl group, or a mycinosyloxymethyl group; $R^5$ represents a methyl group or a methoxy group; $R^6$ represents a hydrogen atom or a methyl group; ⁓ represents a single bond or a double bond; --- represents a single bond, a double bond, or an oxiran-2,3-diyl group; and —·— means that the macrolactone ring forms a 16-membered ring or a 17-membered ring.

Furthermore, according to the present invention, there is further provided a process of producing the above-described derivatives of macrolide compound shown by general formula (1) by reacting the macrolide compound represented by general formula (2)

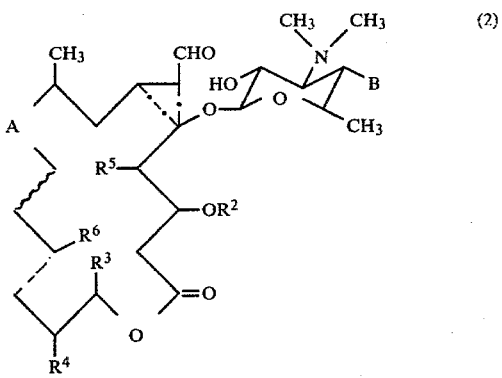

wherein B represents a hydrogen atom, a hydroxyl group, or an acylmycarosyloxy group

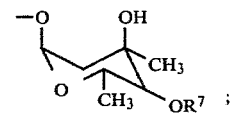

$R^7$ represents an acyl group; and A; $R^2$; $R^3$; $R^4$; $R^5$; $R^6$; ⁓; ---; and —·— have the same significance as in general formula (1), with a diol, a dithiol, or a mercaptoalcohol in the presence of an organic acid and then reacting the reaction product with an oxidizing agent and an acylating agent, successively.

DESCRIPTION OF THE PREFERRED EMBODIMENTS

As the compounds provided by the present invention, there are such macrolide series antibiotics as Leucomycins, Tetrahydroleucomycins, Josamycin, YL-704 group, SF-837 group, Espinomycins, Spiramycins, Malidomycins, Carbomycins, Tylosin, Angoramycin, Cirramycins, Rosamicin, M-4365G₂, etc., from which a part or the whole of the sugar moieties have been released and of which the aldehyde groups have been protected by a cyclic acetal or a thioacetal.

Hitherto, as an aglycone moiety derived from macrolide series antibiotics, there is known the compound having the following formula (J. Antibiot., 27, 147–149(1974))

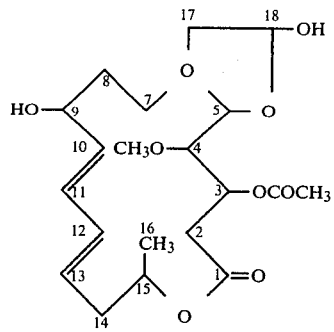

However, as shown supra, because of stabilization due to formation of an intramolecular acetal between the hydroxyl group at the 5-position and the aldehyde group at the 18-position, the compound shows difficulties for producing various derivatives by introduction of various substituents to the hydroxyl group at the 5-position which is the most important position to be substituted by sugar moieties in every macrolide series antibiotics having pharmaceutical activities.

Since, when the compound of this invention is an aglycone, the aldehyde group at the 18-position (in case of 16-membered ring) or the 17-position (in case of 17-membered ring) has been protected by a cyclic acetal or a thioacetal, the adjacent hydroxyl group at the 5-position can exist in the free state and hence other sugars or substituents can be easily introduced into the hydroxyl group. Such a process has not hitherto been known and has first been discovered by the inventors. That is, the invention makes it possible to produce semi-synthesized macrolide series antibiotics and has the feature capable of producing further many useful semi-synthetic macrolides.

As the reaction reagents used for forming cyclic acetals or thioacetals in this invention, there are dihydric alcohols such as ethylene glycol, propylene glycol, 1,3-propanediol, 2,3-butanediol, etc.; dithiols such as 1,2-ethanedithiol, 2-methyl-1,3-propanedithiol, etc., and mercaptoalcohols having both a hydroxyl group and mercapto group such as mercaptoethanol, mercaptopropanol, etc. Furthermore, as the protected aldehyde group formed by the reaction with the aldehyde group, i.e., the cyclic acetal, thioacetal, etc., there are 1,3-dioxolan-2-yl group, 1,3-dithiolan-2-yl group, 1,3-dithian-2-yl group, 1,3-oxathiolan-2-yl group, etc. Moreover, examples of the lower alkyl group and the acyl group in the starting materials and the desired products in this invention are a methyl group, an ethyl group, an acetyl group, a propionyl group, a butyryl group, an isobutyryl group, an isovaleryl group, etc.

Now, the reaction of this invention is shown by the following reaction formula;

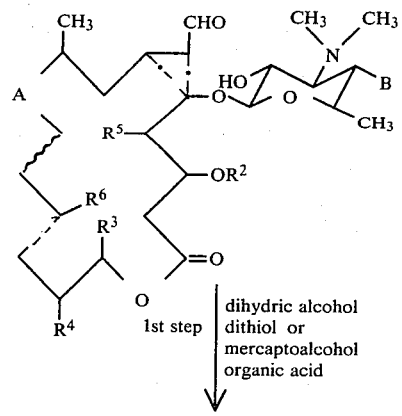

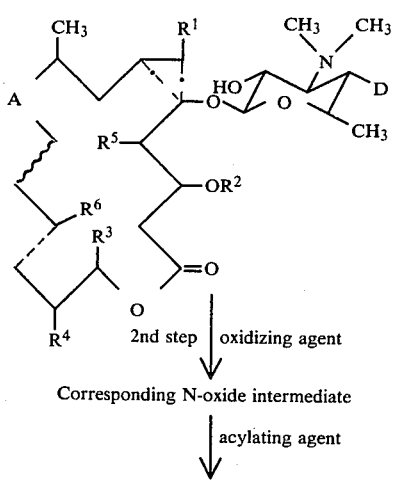

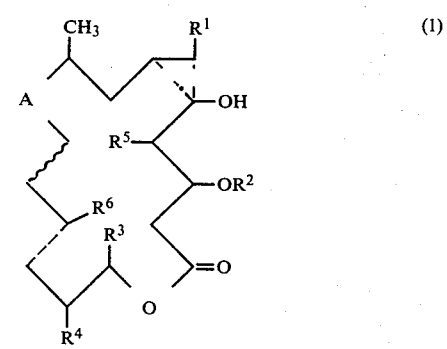

in the above formulae, D represents a hydrogen atom or a hydroxyl group; and A,B, $R^1,R^2,R^3,R^4,R^5$ and $R^6$ have the same significance as above.

The 1st step of the process of this invention, that is the protection of the aldehyde group is performed by reacting the starting material of formula (2) and a dihydric alcohol, a dithiol, or a mercaptoalcohol in the presence of an organic acid in an anhydrous organic solvent such as, for example, acetonitrile, chloroform, etc. The reaction proceeds smoothly at room temperature without heating. Examples of the organic acid used in this reaction are p-toluenesulfonic acid, methanesulfonic acid, etc.

In the reaction of step 1, when group B is an acylmycarosyloxy group, the group is released and is, at the same time, converted into group D (=OH).

The reaction of step 2 is performed by reacting the compound of formula (3) and a conventional oxidizing agent, such as, perbenzoic acid, peracetic acid, in particular m-chloroperbenzoic acid to form the corresponding N-oxide compound and then treating the N-oxide compound with an acylating agent such as acetic anhydride, propionic anhydride, or benzoic anhydride. The reaction is usually performed in an anhydrous organic solvent such as chloroform, carbon tetrachloride, acetonitrile, etc. Also, it is preferred that the reaction be performed at room temperature in the first stage and under heating in the following stage. The N-oxide intermediate formed in the first stage of the reaction may be isolated but may be subjected to the following stage reaction without isolation from the reaction mixture.

The reaction product of formula (1) formed is isolated from the reaction mixture and purified by ordinary procedures such as extraction, column chromatography, preparative thin layer chromatography, etc.

The compounds of formula (3) and formula (1) are both novel compounds and are profitably used as intermediates for producing various macrolide series antibiotics. In particular, since the compound of formula (3) (D=OH) possesses one of two sugar residues usually contained in a macrolide series antibiotics, the compound is useful for studying the relationship between chemical structures and medicinal activity and will contribute to the discovery of other novel antibiotics and further has merit in that other sugar moieties etc., can be comparatively easily introduced into compound on an industrial scale.

For example, the compound of formula (3) (D=OH) is reacted with the compound shown by formula (4).

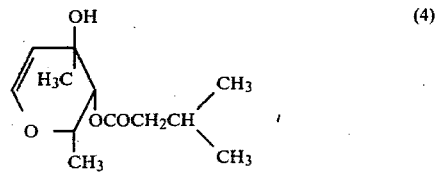

in the presence of a brominating agent and then the product can be converted into a novel antibiotic by releasing the protective group of the aldehyde group. The reaction is shown by the following reaction formula;

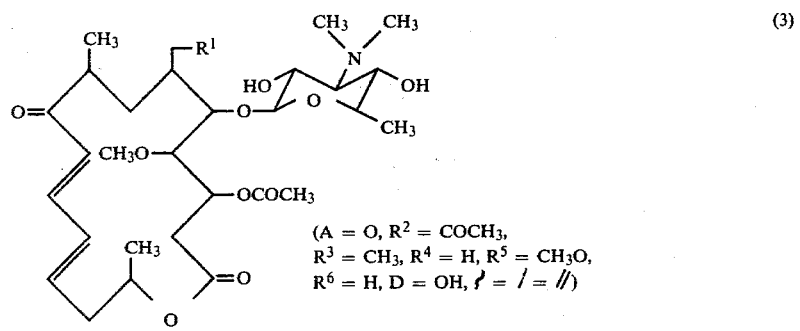

$(A = O, R^2 = COCH_3,$
$R^3 = CH_3, R^4 = H, R^5 = CH_3O,$
$R^6 = H, D = OH, \ell = l = ll)$

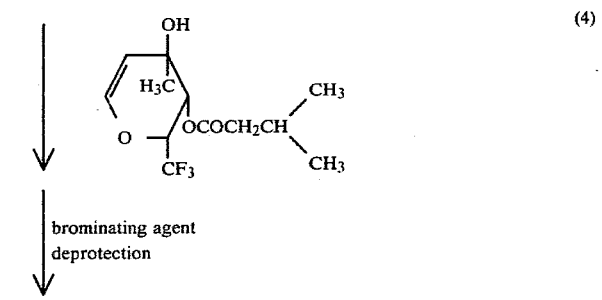

brominating agent
deprotection

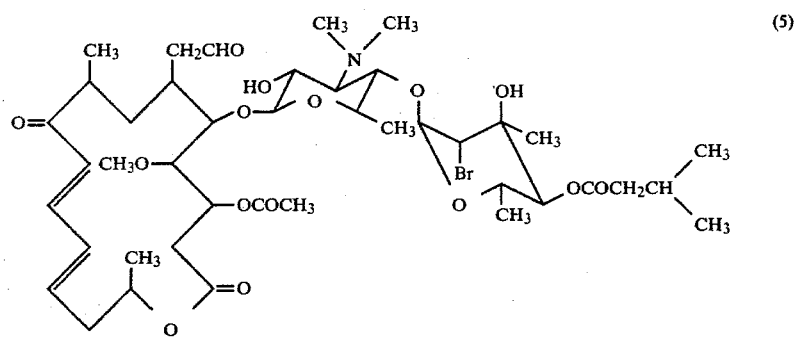

The compound of formula (5) has a structural feature in that it has a bromine atom at the 2-position of the mycarose moiety of Carbomycin B and shows excellent antimicrobial activity against various gram negative bacteria. For example, comparison of the antimicrobial activity of the compound of formula (5) and that of Carbomycin B shows that the compound of formula (5) exhibits the antimicrobial activity of about twice that of Carbomycin B to Streptococcus aureus NBJ, Corynebacteium bovis 1810, Escherichia coli NIHJ, Klebsiella pneumoniae PCI 602, etc.

As the brominating agent used in this reaction, there are 1,3-dibromo-5,5-dimethylhydantoin, N-bromosuccinimide, N-bromophthalimide, N-bromoacetamide, etc., and the brominating agent is usually used in a stoichiometric amount for equimolar amounts of the compound of formula (3) (D=OH) and the compound of formula (4). The reaction is usually performed in an anhydrous organic solvent and examples of the preferred solvents are acetonitrile, benzene, ethyl ether, dimethyl sulfoxide, etc., or mixtures of them. The reaction temperature is below room temperature and, in particular, the temperatures of 0° C. to −20° C. are suitable. The reaction period of time is controlled according to the properties of the solvent and brominating agent employed but is properly from 10 minutes to 48 hours. The reaction product of formula (5) is isolated and purified by ordinary isolation procedures.

EXAMPLE 1

In 25 ml. of anhydrous acetonitrile was dissolved 5.14 g. (6.23 millimoles) of Carbomycin B and after adding to the solution 25 ml. of anhydrous ethylene glycol, 1.60 g. (9.30 millimoles) of anhydrous p-toluenesulfonic acid was added to the mixture with stirring at room temperature followed by allowing to stand for one hour. After the reaction was over, the reaction mixture was neutralized by the addition of 800 mg. (9.52 millimoles) of sodium hydrogencarbonate, the reaction mixture was then poured in 150 ml. of aqueous saturated sodium hydrogencarbonate solution, and the product was extracted twice each time with 250 ml. of ethyl acetate. The ethyl acetate layers recovered were combined, washed twice each time with 100 ml. and then once with 50 ml. of saturated aqueous sodium chloride solution, dried over anhydrous sodium sulfate, and then concentrated to dryness. The concentrate was subjected to a column chromatography using a column packed with 300 g. of Wako gel C 200 (trade name) and a 2:1:1 mixture of ethyl acetate, acetone and ethanol as the developing solvent.

First, fractions containing 2'-hydroxyethyl-4-0-isovalerylmycaroside (crude amount 1.65 g.) emerged and then 2.87 g. of the desired product, Demycarosyl Carbomycin B emerged from the column. The product was re-precipitated from a mixture of acetone and n-hexane to provide 2.56 g. (yield 64.1%) of the colorless solid of the desired product, demycarosyl carbomycin B ethylene acetal.

The physiochemical properties of the product are shown below:

(i). Melting point 102°–106° C.
(ii). $[\alpha]_D^{16°} +13°$ (C 1.3, chloroform)
(iii). Rf value 0.35 (silica gel thin layer chromatography, developing solvent: 2:2:1 mixed solvent of ethyl acetate, acetone and ethanol)
(iv). Elemental analysis for $C_{32}H_{51}NO_{12}$

|  | C | H | N |
| --- | --- | --- | --- |
| Calculated: | 59.89% | 8.01% | 2.18% |
| Found: | 59.84% | 7.91% | 2.06% |

(v). U.V. max. 279 n.m. ($\epsilon$ 23000, methanol)
(vi). N.M.R. (CDCl$_3$, TMS), $\delta$(ppm.)
2.02 (s, 3H, 3-OA$_c$), 2.51 (s, 6H,-N(CH$_3$)$_2$),
3.59 (s, 3H, 4-OMe), 3.82 (m, 4H,

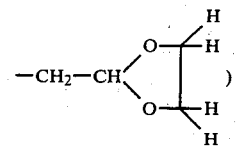

6.3 (d, 1H, J=8.0, 10-H).
(vii). I.R. (CHCl$_3$), cm$^{-1}$
3600, 3450(—OH), 2970(—CH$_3$), 2930(—CH$_2$—),

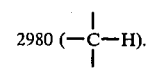

2980 (—C—H).

In addition, 2'-hydroxyethyl-4-0-isovalerylmycaroside in the first effluent was purified by subjecting it to a column chromatography using a column packed with 165 g. of Wako gel C-300 (trade name) and a 3:1 mixture of chloroform and acetone as the developing solvent to provide 1.54 g. (85.7%) of a syrupy mycarose moiety having the following structural formula

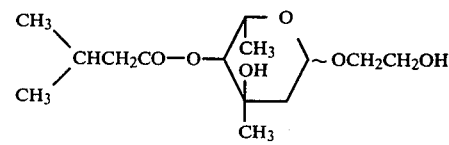

The physiochemical properties of the product are as follows:

(i). $[\alpha]_D^{21} -60°$ (c.1.0, chloroform)
(ii). Rf value 0.26 (silica gel thin layer chromography, developing solvent:
   3:1 benzene-acetone mixture) 0.32 (silica gel thin layer chromatography, developing solvent:
   3:1 chloroform-acetone mixture)
(iii). Elemental analysis for $C_{14}H_{26}O_6$:

|  | C | H |
| --- | --- | --- |
| Calculated: | 57.91% | 9.03% |
| Found: | 58.06% | 8.83% |

EXAMPLE 2

In 25 ml. of anhydrous acetonitrile was dissolved 5.5 g. (6.23 millimoles) of 9-propionyljosamycin (molecular weight 883) and after adding to the solution 25 ml. of anhydrous ethylene glycol, 1.60 g. (9.30 millimoles) of anhydrous p-toluenesulfonic acid was added to the mixture with stirring at room temperature followed by allowing to stand for one hour. After the reaction was over, the reaction mixture was neutralized by the addition of 800 mg (9.52 millimoles) of sodium hydrogencarbonate, carbonate, poured in 150 ml. of saturated aqueous sodium hydrogen-carbonate solution, and extracted twice each time with 250 ml. of etyhl acetate. The ethyl acetate layers recovered were combined, washed twice each time with 100 ml. and once with 50 ml. of saturated aqeous sodium chloride solution, dried over anhydrous sodium sulfate, and concentrated to dryness to provide 5.9 g. of the crude product.

Then, 3.0 g. of the crude product thus obtained was subjected to a column chromatography using a column packed with 150 g. of Wako gel C-200 (trade name) and a 2:1:1 mixture of ethyl acetate, acetone, and ethanol as the eluant. First, 2'-hydroxyethyl-4-0-isovalerylmycaroside emerged and then fractions containing demycarosyl-9-propionyljosamycin ethyleneacetal emerged from the column. The latter was purified by a silica gel column chromatography (packed with Wako gel C-200 (trade name) using a 6:1 mixture of ethyl acetate and methanol as the eluent) concentrated to dryness and re-precipitated from a mixture of acetone and hexane to provide 590 mg. of the white powder of demycarosyl-10-propionyljosamycin ethyleneacetal.

The physiochemical properties of the product are shown below:

(i). Rf value 0.22 (silica gel thin layer chromatography, developing solvent: 2:1:1 ehtyl acetate-acetone-ethanol mixture)

(ii). N.M.R. (CDCl$_3$, TMS), δ(ppm)
2.09 (3H, s, —OCOCH$_3$), 2.52 (6H, s,

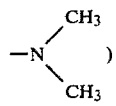
)

3.56 (3H, s, —OCH$_3$), 0.99 (3H, d, J=6.0, >CH<u>CH$_3$</u>)

1.11 (3H, t, J = 8.0 —CH$_2$CH$_3$)

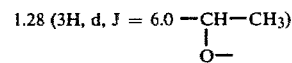

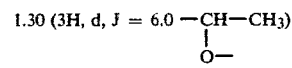

3.81 (2H, m, —OCH$_2$CH$_2$O—)

3.96 (2H, m, —OCH$_2$CH$_2$O—)

(iii). Mass spectrum: m/e 699 (M+)

EXAMPLE 3

In 2.5 ml. of anhydrous acetonitrile was dissolved 525 mg. (0.62 millimole) of Spiramycin I and after adding to the solution 2.5 ml. of anhydrous ethylene glycol, 160 mg. (0.93 millimole) of anhydrous p-toluenesulfonic acid was added to the mixture with stirring at room temperature followed by allowing to stand for one hour. After the reaction was over, the reaction mixture was neutralized by the addition of 80 mg. (0.95 millimole) of sodium hydrogencarbonate, poured in 15 ml. of saturated aqueous sodium hydrogencarbonate solution, and extracted twice each time with 25 ml. of ethyl acetate. The ethyl acetate layers recovered were combined, washed twice each time with 10 ml. and once with 5 ml. of saturated aqueous sodium chloride solution, dried over anhydrous sodium sulfate, and concentrated to dryness. (Crude amount 570 mg.).

Then, 570 mg. of the crude product was subjected to a silica gel column chromatography using a 2:1:1 mixture of ethyl acetate, acetone, and ethanol as the eluant First, fractions containing 2'-hydroxyethylmycaroside emerged and then fractions containing demycarosylspiromycin I ethylene acetal emerged from the column. The latter fractions were combined and concentrated, purified by a silica gel column chromatography using a 6:1 mixture of ethyl acetate and methanol, and re-precipitated from a mixture of acetone and hexane to provide the white powder of demycarosylspiramycin I ethylene acetal. The product showed the Rf value of 0.18 by a silica gel thin layer chromatography (precoated plate (Kiesel gel 60 F-254), developing solvent: a 2:1:1 ethyl acetate-acetone-ethanol mixture).

Also, the nuclear magnetic resonance spectra (CDCl$_3$), δ(ppm) of the product were as follows:

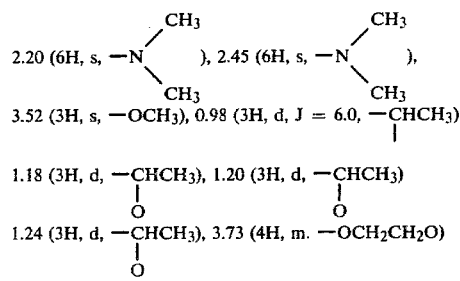

In the hydrolyzate obtained by the treatment with 1% hydrochloric acid for 10 hours, mycarose could not be detected by a thin layer chromatography. Also, in the nuclear magnetic resonance spectra, 9.86 ppm (1H, s, —CHO) disappeared and 3.73 ppm (4H, m,—OCH$_2$CH$_2$0) appeared newly.

EXAMPLE 4

(a) In 30 ml. of anhydrous chloroform was dissolved 2.79 g. (4.34 millimoles) of 3-acetoxy-5-[3,6-dideoxy-3-dimethylamino-β-D-glucopyranosyloxy]-6-(1,3-dioxolan-2-yl)methyl-4-methoxy-8-methyl-9-oxo-10,12-hexadecadien-15-olide, and then 790 mg. (1.05 mole equivalents) of metachloroperbenzoic acid was added to the solution with stirring.

After 10 minutes, the completion of the reaction was confirmed by a thin layer chromatography and then the reaction mixture was concentrated to dryness. The concentrate was subjected to a column chromatography using a silica gel column and a 4:1 mixture of chloroform and methanol as the developing solvent to isolate the reaction product, whereby 2.85 g. of the N-oxide compound was obtained.

(b). In 25 ml. of anhydrous chloroform was dissolved 2.85 g. of the N-oxide compound and after adding thereto 1.35 g. (3 mole equivalents) of acetic anhydride, the mixture was refluxed for one hour.

After the reaction was over, the reaction mixture was allowed to cool to room temperature and then 20 ml. of saturated aqueous sodium hydrogencarbonate solution was added to the reaction mixture to decompose excess acetic anhydride and to neutralize it. Then, the product was extracted once with 100 ml. and twice each time with 50 ml. of chloroform. The extracts were combined washed once with 20 ml. of saturated aqueous sodium chloride solution, and the chloroform layer formed was recovered, dried over anhydrous sodium sulfate, and concentrated to dryness. The concentrate thus formed was subjected to a column chromatography packed with silica gel and a 2:1 mixture of n-hexane and acetone as a developing solvent and the fractions containing the product were collected and concentrated under reduced pressure, whereby 712 mg. of a yellow solid of 3-acetoxy-5-hydroxy-6-(1,3-dioxalan-2-yl)methyl-4- methoxy-8-methyl-9-oxo-10,12-hexadecadien-15-olide was obtained.

Further purification of the product thus obtained to a silica gel column chromatography using a 4:1 mixture of chloroform and acetone and a 1:2 mixture of benzene and ethyl acetate gave a white purified product.

The physicochemical properties of the product are as follows:
(i). Melting point 72°–75° C.
(ii) $[\alpha]_D^{21}$ +10° (c.1.0, chloroform).
(iii). Rf values:
  0.4 (silica gel thin layer chromatography, developing solvent: 1:2 benzene-ethyl acetate mixture),
  0.35 (silica gel thin layer chromatography, developing solvent: 2:1 hexane-acetone mixture), and
  0.4 (silica gel thin layer chromatography, developing solvent 4:1 chloroform-acetone mixture).
(iv). Elemental analysis for $C_{24}H_{36}O_9$:

|  | C | H |
|---|---|---|
| Calculated: | 61.52% | 7.74% |
| Found: | 61.74% | 7.84% |

(v). N.M.R. (CDCl$_3$, TMS), δ(ppm)
  1.20, 1.28 (d, 3H × 2, -CH$_3$ at the 8-position and —CH$_3$ at the 15-position)
  2.02 (s, 3H, —OCOCH$_3$ at the 3-position)
  3.58 (s, 3H, —OCH$_3$ at the 4-position)
  3.7-4.0 (m, 4H,

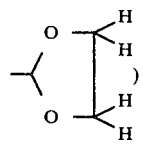

6.35 (d, 1H, H at the 10-position).
(vi). U.V. max.
  279 nm (δ, 22, 100) (methanol)
(vii). I.R. (KBr), cm$^{-1}$
  1730 (ester), 1676, 1630 (double bond).

In addition, when the aforesaid product was reacted with acetic anhydride in pyridine, acicular crystals of a product in which the hydroxyl group at the 5-position of the macrolide ring was acetylated were obtained. The properties of the acetylated product are as follows:
(i). Melting point 220.5°–221.5° C.
(ii). $[\alpha]_D^{21}$ 0 ( c. 10, chloroform)
(iii). Rf value:
  0.4 (silica gel thin layer chromatography, developing solvent: 2:1 hexane-acetone mixture),
(iv). Elemental analysis for $C_{26}H_{38}O_{10}$:

|  | C | H |
|---|---|---|
| Calculated: | 61.16% | 7.50% |
| Found: | 61.18% | 7.48% |

(v). U.V. max.
  279 nm (ε21500) (methanol)

REFERENCE EXAMPLE 1

In 5 ml. of anhydrous nitromethane was dissolved 100 mg. of 3-acetoxy-5-hydroxy-6-(1,3-dioxolan-2-yl) methyl-4-methoxy-8-methyl-9-oxo-10,12-hexadecadien-15-olide obtained in Example 4 (b) and after adding to the solution 303 mg. of mercuric cyanide and 1 g. of Drylite (tradename), the mixture was stirred vigorously. Then 358 mg. (5 mole equivalents) of 2,4-0-diacetyl-1-bromo-1,3,6-trideoxy-3-(dimethylamino)-D-glucose hydrobromide was added to the mixture in five portions over a period of 4 hours at room temperature and after stirring the resultant mixture vigorously for 10 hours, the reaction mixture was poured in 10 ml. of saturated aqueous sodium hydrogencarbonate solution and extracted three times, each time 10 ml. of ether. The ether extracts were combined, washed with water, dried, and concentrated under reduced pressure. The residue obtained was subjected to a silica gel column chromatography using a 2:1 mixture of hexane and acetone as the eluent to provide 78 mg. of a solid containing the reaction product. The product was further subjected to a silica gel column chromatography using a 1:3 mixture of chloroform and ethyl acetate as the eluant and furthermore the product emerging from the column was subjected to a silica gel column chromatography using a mixture of chloroform and acetone as the eluant. Then, the solid product obtained was re-precipitated from a mixture of ether and hexane to provide 24 mg. of the colorless solid of 3-acetoxy-5-[2,4-0-diacetyl-1,3,6-trideoxy-3-dimethylamino-3-D-glucopyranosyloxy]-6-[1,3-dioxolan-2-yl]methyl-4-methoxy-8-methyl-9-oxo-10,12-hexadecadien-15-olide.

The physicochemical properties of the product are as follows:
(i). Melting point 103°–110° C.
(ii). $[\alpha]_D^{20}$ −14° (c. 1.0, chloroform)
(iii). N.M.R. (CDCl$_3$, TMS), δ(ppm)
  1.13, 1.18, 1.29 (each d, 3H×3, CH$_3$ at the 5'-position, CH$_3$ at the 8-position, and CH$_3$ at the 15-position)
  ~2.04 (each s, 3H×3, CH$_3$COO— at the 3-position, CH$_3$COO at the 2'-position, CH$_3$COO—at the 4'-position),
  2,35 (s, 3H×2,

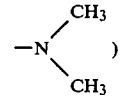

3.54 (s, 3H, CH$_3$O-at the 4-position)
  6.32 (d, 1H, H at the 10-position).
(iv). U.V. max.
  279 nm (ε, 23,000) (methanol)
(v). I.R. (CHCl$_3$) cm$^{-1}$
  ~2950 (CH), ~1740 (ester),
  1675, 1640 (double bond)
(vi). Elemental analysis for $C_{36}H_{55}NO_{14}$:

|  | C | H | N |
|---|---|---|---|
| Calculated: | 59.57% | 7.64% | 1.93% |
| Found: | 59.34% | 7.55% | 1.81% |

EXAMPLE 5

(a). In 8.2 ml. of anhydrous chloroform was dissolved 818 mg. (1.28 millimoles) of 5-(3,6-dideoxy-3-dimethylamino-β -D-glucopyranosyloxy)-6-(1,3-dioxolan-2-yl)methyl-3-hydroxy-14-hydroxymethyl-4,8,12-trimethyl-9-oxo-10,12-heptadecadien-15-olide and then 231 mg. (1.34 millimoles ) of metachloroperbenzoic acid was added with stirring under ice-cooling. After 5 minutes, the temperature of the reaction mixture was allowed to reach room temperature and the reaction was continued as it was for 15 minutes. After confirming the end of the reaction, the reaction mixture was concentrated to dryness. The concentrate was subjected to a silica gel column chromatography using a column packed with 80 g. of Wako gel C-200 (trade name) and a 5:1 mixture of chloroform and methanol as developing solvent to provide 840 mg. (yield 100%) of the corresponding N-oxide compound.

The physicochemical properties of the product are as follows:

(i). $[\alpha]_D^{25} + 9°$ (c, 1.0, chloroform)

(ii). Rf value: 0.29 (silica gel thin layer chromatography, developing solvent: 7:1 chloroform-methanol mixture)

(iii). N.M.R. (CDCl$_3$, TMS), (ppm)
  1.85 (3H, s, —CH$_3$ at the 12-position)
  3.31 (3H, s )
  3.55 (3H, s)
  3.92 (4H, m,

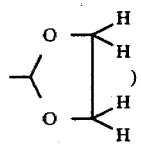

)

4.50 (1H, d, J=6 Hz, at the 1'-position)
  5.91 (1H, d, J=11 Hz, H at the 13-position)
  6.17 (1H, d, J=16 Hz, H at the 11-position)
  7.28 (1H, d, J=16 Hz, H at the 10-position).

(iv). U.V. max.
  282 nm ($\epsilon$, 23,000) (methanol)

(v). I.R. cm$^{-1}$
  2960 ( —CH$_3$ ), 2920 ( —CH$_2$—), 1735 (lactone)
  1680 (ketone), 1600 (diene), 950 ( N→O )

(vi.) Elemental analysis for C$_{33}$H$_{55}$NO$_{12}$:

|  | C | H | N |
|---|---|---|---|
| Calculated: | 60.26% | 8.43% | 2.13% |
| Found: | 60.32% | 8.54% | 2.02% |

(b). In 7.5 ml. of anhydrous chloroform was dissolved 745 mg. (1.13 millimoles) of the N-oxide compound obtained in the above step and after adding to the solution 0.32 ml. (3.39 millimoles) of acetic anhydride, the mixture was refluxed on an oil bath at 80° C. After 90 minutes, the consumption of the starting material was confirmed and then 7 ml. of saturated aqueous sodium hydrogencarbonate solution was added to the reaction mixture followed by stirring for one hour at room temperature. To the mixture was added 30 ml. of chloroform and an aqueous layer formed was separated and further extracted twice each time with 15 ml. of chloroform. The chloroform extracts were combined, washed with 14 ml. of saturated aqueous sodium chloride solution and then with 14 ml. of water, dried over anhydrous sodium sulfate, and concentrated to dryness. The concentrate was subjected to a column chromatograhy using a column packed with 70 g. of Wako gel C-200 (trade name) and a 3:1 mixture of benzene and acetone as the developing solent to provide 222 mg. (yield 42%) of 6-(1,3-dioxolan-2-yl)methyl-3,5-dihydroxy-14-hydroxymethyl-4,8,12-trimethyl-9-oxo-10,12-heptadecadien-15-olide. When the product was recrystallized from a mixture of acetone and hexane, colorless acicular crystals were obtained.

The physicochemical properties of the product are as folows:

(i). Melting point 95°–96° C.

(ii). $[\alpha]_D^{25} - 3°$(c. 10, chloroform)

(iii). Rf value: 0.27 (silica gel thin layer chromatography, developing solvent: 3:1 benzene-acetone mixture)

(iv). Elemental analysis for C$_{25}$H$_{40}$O$_8$:

|  | C | H |
|---|---|---|
| Calculated: | 64.08% | 8.60% |
| Found: | 64.36% | 8.35% |

(v). N.M.R. (CDCl$_3$, TMS), $\delta$(ppm)
  1.02 (3H, d, J=6 Hz,—CH$_3$ at the 4-position)
  1.25 (3H, d, J=9 Hz, —CH$_3$ at the 8-position)
  1.99 (3H, s, —CH$_3$ at the 12-position)
  3.87 (4H, m,

)

3.98 (2H, d, J=5 Hz, —CH$_2$— at the 14-position)
  about 5.0

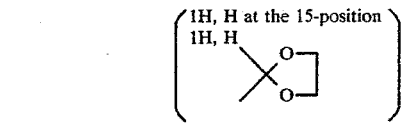

5.99 (1H, d, J=11 Hz, H at the 13-position)
  6.40 (1H, d, J=16 Hz, H at the 11-position)
  7.42 (1H, d, J=16 Hz, H at the 10-position)

(vi). U.V. max
  282 n m ($\epsilon$, 13,000) (methanol)

(vii). I.R. (KBr), cm$^{-1}$
  2980 (—CH$_3$), 2930 (—CH$_2$—), 1735 (lactone),
  1680 (ketone), 1600 (diene).

PREPARATION OF THE STARTING MATERIAL (a). To 7.7 g. (8.4 millimoles) of Tylosin was added 7.7 ml. of water and after adding to the mixture 1.5 mole equivalents (2.4 g.; 12.6 millimoles) of p-toluenesulfonic acid, the resultant mixture was refluxed for 3.5 hours. After confirming the end of the reaction by a thin layer chromatography, a tarry material which had separated was washed twice each time with 60 ml. of chloroform and discarded. The remaining aqueous layer was thoroughly mixed with 2.1 g of sodium hydrogencarbonate and was extracted twice each time with 60 ml. of chloroform. The chloroform washings and extracts were combined, washed once with 40 ml. of water, dried over anhydrous sodium sulfate, and concentrated to dryness.

By subjecting the oily material obtained to a silica gel column chromatography using a column packed with 130 g. of Wako gel C-200 (trade name) and a 5:1 mixture of chloroform and methanol as the developing solvent, 1.85 g. (yield 40%) of 5-(3,6-dideoxy-3-dimethylamino-β-D-glucopyranosyloxy)-6-formylmethyl-3-hydroxy-14-hydroxymethyl-4,8,12-trimethyl-9-oxo-10,12-heptadecadien-15-olide was obtained as a colorless solid.

The physicochemical properties of the product are as follows:

(i). Rf value: 0.31 (silica gel thin layer chromatography, developing solvent: 1:2 chloroform-menthanol mixture)

(ii). N.M.R. (CDCl$_3$, TMS), β(ppm)
1.83 (3H, s, —CH$_3$ at the 12-position)
2.54 (6H, s, —N(CH$_3$)$_2$ at the 3'-position)
3.77 (2H, d, J=6 Hz, —CH$_2$— at the 14-position)
4.28 (1H, d, J=7 Hz, H at the 1'-position)
5.00 (1H, m. H at the 15-position)
5.90 (1H, d, J=11 Hz, H at the 13-position)
6.30 (1H, d, J=16 Hz, H at the 11-position)
7.36 (1H, d, J=16 Hz, H at the 10-position)
9.75 (1H, —CHO)

(iii). I.R. (KBr), cm$^{-1}$
2960 (—CH$_3$), 2920 (—CH$_2$—), 2810, 2770, 2730 (—N(CH$_3$)$_2$), 1735 (lactone),
1680 (ketone), 1600 (diene).

(b). After dissolving 1.14 g. (1.92 millimoles) of the compound in aforesaid step (a) in 5.7 ml. of acetonitrile, 5.7 ml. of ethylene glycol was added to the solution. Then, 494 mg. (2.87 millimoles) of p-toluenesulfonic acid was added to the mixture with stirring at room temperature and the reaction was carried out for 3 hours. After the reaction was over, 483 mg. (5.75 millimoles) of sodium hydrogencarbonate was added to the mixture and after stirring for one hours, the reaction mixture was poured in 34 ml. of saturated aqueous sodium hydrogencarbonate solution. Then, the reaction mixture was extracted twice each time with 57 ml. of chloroform and the chloroform extracts were combined, washed with 14 ml. of saturated aqueous sodium chloride solution and then 28 ml. of water, dried over anhydrous sodium sulfate, and then concentrated to dryness.

The concentrate was subjected to a column chromatography using a column packed with 40 g. of Wako gel C-200 (trade name) and a 5:1 mixture of chloroform and methanol to provide 1.18 g. (yield 96%) of 5-(3,6-dideoxy-3-dimethylamino-β-D-glucopyranosyloxy)-6-(1,3-dioxolan-2-yl)-methyl-3-hydroxy-14-hydroxymethyl-4,8,12-trimethyl-9-oxo-10,12-heptadecadien-15-olide as a colorless solid. By recrystallization from a mixture of acetone and hexane, colorless acicular crystals of the product were obtained.

The physicochemical properties of the product are as follows:

(i). Melting point 226°-230° C.
(ii). $[α]_D^{25°}$ −7° (c. 1.0, chloroform)
(iii). Rf value: 0.38 (silica gel thin layer chromatography, developing solvent: 5:1 chloroform-methanol mixture)
(iv). Elemental analysis for C$_{33}$H$_{55}$NO$_{11}$:

|  | C | H | N |
|---|---|---|---|
| Calculated: | 61.76% | 8.64% | 2.18% |
| Found: | 61.51% | 8.47% | 2.16% |

(v). M.M.R. (CDCl$_3$, TMS), δ(ppm)
1.83 (3H, s, —CH$_3$ at the 12-position)
2.54 (6H, s, —N(CH$_3$)$_2$ at the 3'-position)

3.86 (4H, m,

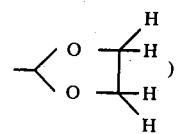
)

4.34 (1H, d, J=6 Hz, H at the 1'-position) about 5.0

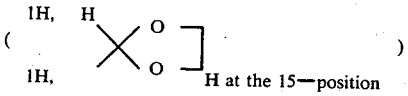

5.87 (1H, d, J=11 Hz, H at the 13-position)
6.27 (1H, d, J=16 Hz, H at the 11-position)
7.35 (1H, d, J=16 Hz, H at the 10-position)
(vi). U.V. max.
282 nm (ε, 26,000) (methanol)
(vii). I.R. (KBr) cm$^{-1}$
2960 (CH$_3$), 2920 (—CH$_2$—), 2810, 2770, 2730 (—N(CH$_3$)$_2$), 1735 (lactone), 1685 (ketone), 1600 (diene).

EXAMPLE 6

In 9.2 ml. of anhydrous chloroform was dissolved 926 mg. (1.40 millimoles) of 3-acetoxy-5-(3,6-dideoxy-3-dimethylamino-D-glucopyranosyloxy)-9-hydroxy-4-methoxy-8-methyl-6-(4-methyl-1,3-dioxolan-2-yl)methyl-15-hexadecanolide and then 265 mg. (1.54 millimoles) of m-chloroperbenzoic acid was added to the solution with stirring under ice-cooling. After 5 minutes, the temperature of the reaction mixture was allowed to return to room temperature and stirred for 30 minutes at the temperature. After the reaction was over, the reaction mixture was concentrated to dryness and the residue was subjected to a column chromatography using a column packed with 50 g. of Wako gel C-200 (trade name) and a 7:1 mixture of chloroform and methanol as the developing solvent to provide 923 mg. (yield 97%) of the corresponding N-oxide compound.

The physicochemical properties of the product are as follows:

(i). $[α]_D^{25°}$ +4° (c. 1.0, chloroform)
(ii). Rf value: 0.37 (silica gel thin layer chromatography, developing solvent: 10:1 chloroform-methanol mixture)
(iii). Elemental analysis for C$_{33}$H$_{59}$NO$_{13}$:

|  | C | H | N |
|---|---|---|---|
| Calculated: | 58.48% | 8.77% | 2.07% |
| Found: | 58.64% | 8.53% | 2,14% |

(iv). N.M.R. (CDCl$_3$, TMS), δ(ppm)
2.20 (3H, s, —OCOCH$_3$ at the 3-position)
3.30 (3H, s)
3.50 (3H, s)
3.61 (3H, s, —OCH$_3$ at the 4-position)
4.56 (1H, d, J=7 Hz, at the 1'-position)
5.28 (1H, m, H at the 3-position).
(v). I.R. (KBr) cm$^{-1}$
2960 (CH$_3$), 2925 and 2850 (—CH$_2$—),
1735 (lactone), 960 (N→O).

(b). In 8.4 ml. of anhydrous chloroform was dissolved 841 mg. (1.24 millimoles) of the N-oxide compound obtained in the above step and after adding to the solution 0.35 ml. (3.7 millimoles) of acetic anhydride, the mixture was refluxed for 60 minutes on an oil bath at 80° C. After confirming the end of the reaction, 8.4 ml. of saturated aqueous sodium hydrogencarbonate solution was added to the reaction mixture followed by stirring for 60 minutes.

The aqueous layer formed was separated and further extracted with 25 ml. and then 12 ml. of chloroform. The chloroform solvents were combined, washed with 17 ml. of saturated aqueous sodium chloride solution and then water, dried over anhydrous sodium sulfate, and concentrated to dryness. The residue was subjected to a column chromatography using a column packed with 80 g. of Wako gel C-300 (trade name) and a 4:1 mixture of benzene and acetone as the developing solvent to provide 222 mg. (yield 37%) of 3-acetoxy-5,9-dihydroxy-4-methoxy-8-methyl-6-(4-methyl-1,3-dioxclan-2-yl)methyl-15-hexadecanolide.

The physicochemical properties of the product are as follows:

(i) $[\alpha]_D^{25°}$ −19° (c. 1.0, chloroform)

(ii). Rf value: 0.29 (thin layer chromatography, developing solvent: 4:1 benzene-acetone mixture)

(iii). Elemental analysis for $C_{25}H_{44}O_9$:

|  | C | H |
|---|---|---|
| Calculated: | 61.45% | 9.08% |
| Found: | 61.28% | 8.84% |

(iv). N.M.R. (CDCl$_3$, TMS), δ(ppm)
 0.98 (3H, d, J=6 Hz,—CH$_3$ at the 8-position)
 2.20 (3H, s, OCOCH$_3$ at the 3-position)
 3.66 (3H, s, —OCH$_3$ at the 4-position)

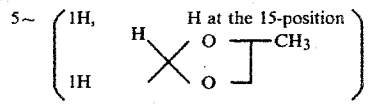

5.36 (1H, m, H at the 3-position)
(v). I.R. (KBr) cm$^{-1}$
 2960 (CH$_3$), 2925 and 2850 (—CH$_2$—), 1735 (lactone).

In addition, the starting material used in the process of Example 6 can be obtained by the following process.

PREPARATION OF THE STARTING MATERIAL

After dissolving 1.66 g. (2.00 millimoles) of 3-acetoxy-5-[3,6-dideoxy-4-O-(2,6-dideoxy-4-O-isovaleryl-3-C-methyl-α-L-altropyranosyl)-3-dimethylamino-β-D-glucopyranosyloxy]-6-formylmethyl-4-methoxy-8-methyl-9-hydroxy-hexadecanolide in 8.3 ml. of anhydrous acetonitrile, 4.2 ml. of anhydrous propylene glycol (1,2-propanediol) was added to the solution and further 516 mg. (3.00 millimoles) of anhydrous p-toluenesulfonic acid was added to the mixture with stirring at room temperature. After 2 hours, the end of the reaction was confirmed and 504 mg. (6.00 millimoles) of sodium hydrogencarbonate was added to the reaction mixture followed by stirring for one hour. Then, 50 ml. of saturated aqueous sodium hydrogencarbonate solution was added to the reaction mixture and the product was extracted twice each time with 83 ml. of chloroform. The chloroform layers were combined washed twice each time with 42 ml. of saturated aqueous sodium chloride solution and once with 83 ml. of water, dried over anhydrous sodium sulfate, and then concentrated to dryness.

By subjecting 80 g. of the residue to a column chromatography using a column packed with Wako gel C-200 (trade name) and a 10:1 mixture of chloroform and methanol as the developing solvent, 1.29 g. (yield 98%) of 3-acetoxy-5-(3,6-dideoxy-3-dimethylamino-β-D-glucopyranosyloxy)-9-hydroxy-4-methoxy-8-methyl-6-(4-methyl-1,3-dioxolan-2-yl)methyl-15-hexadecanolide was obtained.

The physicochemical properties of the product are as follows:

(i). $[\alpha]_D^{25°}$ −10° (c. 0.86, chloroform)

(ii). Rf value: 0.37 (silica gel thin layer chromatography, developing solvent: 10:1 chloroform-methanol mixture)

(iii). Elemental analysis for $C_{33}H_{59}NO_{12}$:

|  | C | H | N |
|---|---|---|---|
| Calculated: | 59.89% | 8.99% | 2.12% |
| Found: | 60.18% | 8.70% | 2.02% |

(v). N.M.R. (CDCl$_3$, TMS), δ(ppm)
 2.10 (3H, s, —OCOCH$_3$ at the 3-position)
 2.56 (6H, s, —N(CH$_3$)$_2$ at the 3'-position)
 3.60 (3H, s, —OCH$_3$ at the 4-position)
 4.53 (1H, d, J=7 Hz, H at the 1'-position)
 5∼ (1H, m, H at the 15-position)
 5.30 (1H, m, H at the 3-position)
(v). I.R. (KBr) cm$^{-1}$
 2960 (CH$_3$), 2925 and 2850 (—CH$_2$—), 1735 (lactone).

EXAMPLE 7

In 9.7 ml. of a 1:1 mixture of anhydrous benzene and acetonitrile were dissolved 477 mg. (0.744 millimole) of 3-acetoxy-5-[3,6-dideoxy-3-dimethylamino-β-D-glucopyranosyhoxy]-6-(1,3-dioxolan-2-yl)methyl-4-methoxy-8-methyl-9-oxo-10,12-hexadecadien-15-olide and 169.6 mg. (0.744 millimole) of 4-O-isovalerylmycaral and then 106.4 mg. (0.372 millimole) of 1,3-dibromo-5,5-dimethylhydantoin was added to the solution with stirring at -20° C. followed by further stirring for 4 hours at the temperature. The reaction mixture was allowed to return to room temperature and concentrated under reduced pressure. The residue was dissolved in 50 ml. of chloroform and the solution was washed twice each time with 10 ml. of saturated aqueous sodium hydrogencarbonate solution, dried over anhydrous sodium sulfate, and then concentrated under reduced pressure.

The residue was subjected to column chromatography using a column packed with 15 g. of Wako gel C-300 (trade name) and a 1:1 mixture of benzene and ethyl acetate as the developing solvent to provide 89.7 mg. of a crude reaction product. The product was then subjected to a column chromatography using a column packed with 2 g. of Wako gel C-300 (trade name) and a 1:1 mixture of benzene and ethyl acetate as the developing solvent and further purified by a column chromatography using a column packed with 6 ml. of Sephadex LH 20 (trade name) and a 4:1 mixture of benzene and ethyl acetate. . The product was recrystallized from a mixture of ether and n-hexane to provide 72 mg. (yield 10.2%) of the reaction product, 3-acetoxy-5-[3,6-dideoxy-4-O-(2,6-dideoxy-2-bromo-4-O-isovaleryl-3-C- methyl-α-L-altropyranosyl)-3-dimethylamino-β-D-glucopyranosyloxy]-6-(1,3-dioxolan-2-yl)-methyl-4-methoxy-8-methyl-9-oxo-10,12-hexadecadien-15-olide.

The physicochemical properties of the product are as follows:

(i). Melting point 194°–196° C.
(ii). $[\alpha]_D^{16} -18°$ C. (C 1.2, chloroform)
(iii). Rf value: 0.29 (silica gel thin layer chromatography, developing solvent: 1:1 benzene-ethyl acetate mixture)
(iv). Elemental analysis for $C_{44}H_{70}NO_{16}Br$:

|  | C | H | N |
|---|---|---|---|
| Calculated: | 55.69% | 7.44% | 1.48% |
| Found: | 56.02% | 7.52% | 1.58% |

(v). U.V. max 279 nm (ε, 23,000) (solvent: methanol)
(vi). N.M.R. (CDCl$_{32}$ TMS), δ (ppm)
   0.99 (d, 6H, J=6.0 —CH$_2$CH(CH$_3$)$_2$)), 2.51 (s, 6H, —N(CH$_3$)$_2$), 3.80 (m, 4H,

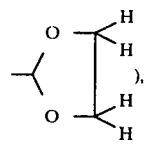

), 3.9∼(m, 1H, 5″—H), 3.98 (d, 1H, J=0.9, 2″-H), 5.22 (d, 1H, J=0.9, 1″—H).
(vii). I.R. (CHCl$_3$) cm$^{-1}$
   3600 and 3450 (—OH), 2970 (—CH$_3$), 2930 (—CH$_2$—),

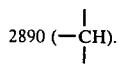

In addition, the aforesaid column chromatography was continued using a 6:3:2 mixture of dichloromethane, ethanol, and ethyl acetate in place of the developing solvent used in the above procedure. The solid product obtained from the effluent was dissolved in 7 ml. of ethyl acetate, and the solution obtained was washed with 2 ml. of saturated aqueous sodium hydrogencarbonate and 2 ml. of water, dried over anhydrous sodium sulfate, and concentrated to dryness. The solid residue obtained was subjected to a column chromatography using a column packed with 38 g. of Wako gel C-300 (trade name) and a 2:1:1 mixture of ethyl acetate, ethanol, and acetone, whereby 314 mg. of the starting material was recovered (yield 65.8%).

EXAMPLE 8

In an ice bath was immersed 37.9 mg. (0.0399 millimole) of the product obtained in Example 7, 3-acetoxy-5-[3,6-dideoxy-4-O-(2,6-dideoxy-2-bromo-4-O-isovaleryl-3-C-methyl-α-L-altropyransoyl)-3-dimethylamino-β-D-glucopyranosyloxy]-6-(1,3-dioxolan-2-yl)methyl-4-methoxy-8-methyl-9-oxo-10,12-hexadecadien-15-olide and after adding thereto 0.23 ml. of a 90% trifluoroacetic acid aqueous solution cooled beforehand with ice-water, the mixture was stirred for 15 minutes. To the mixture was added 310 mg. (3.69 millimoles) of sodium hydrogencarbonate and then the resultant mixture was stirred for 15 minutes.

The reaction mixture was extracted with 4 ml. and 2 ml. of chloroform successively and the extracts were combined and washed with 2 ml. of water, dried over anhydrous sodium sulfate, and concentrated in vacuum. The residue was, first, subjected to a column chromatography using a column packed with 2.5 g. of Wako gel C-300 (trade name) and a 1:1 mixture of benzene and ethyl acetate as a developing solvent and further subjected to a column chromatography using a column packed with 6 ml. of Sephadex LH-20 (trade name) and 1:1 mixture of benzene and ethyl acetate as the developing solvent. By recrystallizing the reaction product from a mixture of ether and n-hexane, 32.5 mg. (yield 90%) of the rosette crystals of 3-acetoxy-5-[3,6-dideoxy-4-O-(2,6-dideoxy-2-bromo-4-O-isovaleryl-3-C-methyl-α-L-altropyranosyl)-3-dimethylamino-β-D-glucopyranosyloxy]-6-formylmethyl-4-methoxy-8-methyl-9-oxo-10,12-hexadecadien-15-olide were obtained.

The physicochemical properties of the reaction product are as follows:

(i). Melting point 172°–174° C.
(ii). $[\alpha]_D^{21} -20°$ (c.1.0, chloroform)
(iii). Rf value: 0.34 (silica gel thin layer chromatography, developing solvent 1:1 benzene-ethyl acetate mixture)
(iv). Elemental analysis for $C_{42}H_{66}NO_{15}Br$:

|  | C | H | N |
|---|---|---|---|
| Calculated: | 55.75% | 7.35% | 1.54% |
| Found: | 55.94% | 7.38% | 1.49% |

(v). U.V. max 279 nm (ε, 23,000), (methanol)
(vi). N.M.R. (CDCl$_3$, TMS), δ(ppm)
   0.98 (d, 6H, J=6.0, —CH$_2$CH(CH$_3$)$_2$)
   2.50 (s, 6H, —N(CH$_3$)$_2$)
   3.98 (d, 1H, J=0.9, 2″-H)
   5.18 (d, 1H, J=0.9, 1″-H)
   6.29 (d, 1H, J=8.0, 10″—H)
   9.56 (s, 1H, —CHO)
(vii). I.R. (CHCl$_3$) cm$^{-1}$ 3600 and 3450 (—OH), 2960 (—CH$_3$), 2930 (—CH$_2$—),

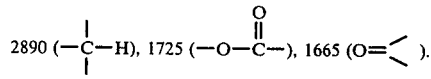

EXAMPLE 9

In 9.7 ml. of a 1:1 mixture of acetonitrile and benzene were dissolved 750 mg. (1.10 millimoles) of 3-acetoxy-5-[3,6-dideoxy-3-dimethylamino-β-D-glucopyranosyloxy]-6-(1,3-dioxolan-2-yl)methyl-4-methoxy-8-methyl-9-oxo-10,12-hexadecadien-15-olide and 266 mg. (1.10 millimoles) of 4-O-isovaleryl cladinal and after adding to the solution of 157 mg. (0.55 millimole) of 1,3-dibromo-5,5-dimethylhydantoin at −20° C., the temperature of the mixture was left to rise to room temperature in a period of 4 hours. The reaction mixture was concentrated under reduced pressure and the concentrate was transferred to a separating funnel with 20 ml. of ethyl acetate. The mixture was washed twice each time with 5 ml. of saturated aqueous sodium hydrogencarbonate solution and then twice each time with 5 ml. of water, dried over anhydrous sodium sulfate, and concentrated under reduced pressure.

The residue was subjected to a column chromatography using a column packed with 10 g. of Wako gel C-300 (trade name) and a 5:1 mixture of chloroform and acetone as the developing solvent to provide 460 mg. of a crude reaction product. The product was then subjected to a column chromatography using a column packed with 28 ml. of Amberlite CG 50 (H+) (tradename) and methanol as the developing solvent to adsorb the product, impurities were eluted out with 70 ml. of methanol, then the product was eluted with a 0.2 N acetic acid methanolic solution, and the eluate was concentrated. The residue obtained as acetate was dissolved in 5 ml. of ethyl acetate, the solution was washed with 2 ml. of saturated aqueous sodium hydrogencarbonate solution and then twice each time with 1 ml. of water, dried over anhydrous sodium sulfate, and concentrated under reduced pressure to provide 157.5 mg. of a purified reaction product.

The purified product was further purified by a column chromatography using a silica gel column packed with 16 g. of Wako gel C-300 (trade name) and a 5:1 mixture of chloroform and acetone as the developing solvent to provide 142 mg (yield 13.5%) of pure 3-acetoxy-5-[3,6-dideoxy-4-O-(2,6-dideoxy-2-bromo-4-O-isovaleryl-3-O-methyl-3-C-methyl-α-L-altropyranosyl)-3-dimethylamino-β-D-glucopyranosyloxy]-6-(1,3-dioxolan-2-yl)methyl-4-methoxy-8-methyl-9-oxo-10,12-hexadecadien -15-olide. The product obtained by re-precipitating it from a mixture of ether and hexane shows the following physicochemical properties:

(i). Melting point 108°-113° C.
(ii). [E]$_D^{16}$ −24.5° (C. 1.0, chloroform)
(iii). Rf value: 0.35 (silica gel thin layer chromatography, developing solvent: 5:1 chloroform-acetone mixture)
(iv). Elemental analysis for C$_{45}$H$_{72}$NO$_{16}$Br:

|  | C | H | N |
| --- | --- | --- | --- |
| Calculated: | 56.13% | 7.54% | 1.45% |
| Found: | 55.89% | 7.55% | 1.38% |

(v). U.V. max 279 nm (ε, 23,000) (methanol)
(vi). N.M.R. (CDCl$_3$, TMS), δ(ppm)
0.96 (d, 6H, J=6.0, —CH$_2$CH(C$\underline{H}_3$)$_2$)
1.34 (d, 3H, J=5.0, 6″—CH$_3$), 2.54 (s, 6H, —N(CH$_3$)$_2$)
3.60 (s, 3H, 4—OCH$_3$),
3.78 (m, 4H,

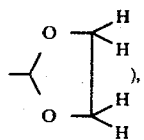
), 5.17 (d, 1H, J=0.8, 1″—H).
(vii). I.R. (CHCl$_3$) cm$^{-1}$
3400 (OH), 2960 (CH$_3$), 2930 (—CH$_2$—),

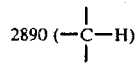

EXAMPLE 10

To 44.4 mg (0.0462 millimole) of the reaction product obtained in Example 9 was added 0.27 ml. of a 90% trifluoroacetic acid aqueous solution under ice-cooling and after stirring the mixture for 15 minutes, the mixture was neutralized by the addition of 358 mg. of sodium hydrogencarbonate powder. Furthermore, the product was completely neutralized by adding 2 ml. of an aqueous sodium hydrogencarbonate solution and extracted thrice each with 2 ml. of ethyl acetate. The extracts were combined, washed three times, each time with 1 ml. of water, dried over anhydrous sodium sulfate, and concentrated under reduced pressure.

The residue was subjected to a column chromatography using a column packed with 5 g. of Wako gel C-300 and a 5:1 mixture of chloroform and acetone as the developing solvent to provide 38.6 mg. (yield 91.0%) of 3-acetoxy-5-[3,6-dideoxy-4-O-(2,6-dideoxy-2-2-bromo-4-O-isovaleryl-3-O-methyl-3-C-methyl-α-L-altropyranosyl)-3-dimethylamino-β-D-glucopyranosyloxy]-6-formylmethyl-4-methoxy-8-methyl-9-oxo-10,12-hexadecadien-15-olide.

The product obtained by re-precipitation from a mixture of acetone and hexane has the following physicochemical properties:

(i). Melting point 118°-122° C.
(ii). [β]$_D^{16}$ − 40.9° (C, 1.0, chloroform)
(iii). Rf value: 0.37 (silicagel thin layer chromatography, developing solvent: 5:1 chloroform-acetone mixture)
(vi). Elemental analysis for C$_{43}$H$_{68}$NO$_{15}$Br:

|  | C | H | N |
| --- | --- | --- | --- |
| Calculated: | 56.20% | 7.46% | 1.52% |
| Found: | 55.97% | 7.38% | 1.49% |

(v). U.V. max 279 nm (ε, 23,000) (methanol)
(vi). N.M.R. (CDCl$_3$, TMS), δ(ppm)
0.98 (d, 6H, J=6.0, CH$_2$CH(C$\underline{H}_3$)$_2$)
2.58 (s, 6H, N(CH$_3$)$_2$), 3.60 (s, 3H, 4—OCH$_3$),
4.24∼(d, 1H, J=0.8, 2″—H),
5.16 (d, 1H, J=0.8, 1″—H), 6.3 (d, 1H, J=8.0, 10—H).
(vii). I.R. (CHCl$_3$) cm$^{-1}$
3450 (—OH), 2960 (—CH$_3$), 2930 (—CH$_2$),

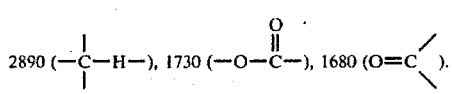

What is claimed is:

1. The aglycone of a macrolide compound represented by the formula

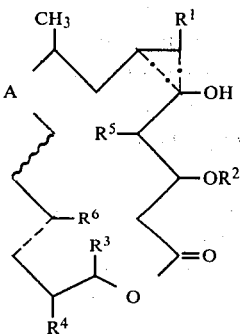

wherein A represents a carbonyl group or

group; R represents a member selected from the group consisting of a hydrogen atom, an acetyl group, a propionyl group, a butyl group, an isobutyl group and an isovaleryl group, or a forosaminyl group; $R^1$ represents an aldehyde group protected by a cyclic acetal or thioacetal; $R^2$ represents a hydrogen atom or an acyl group; $R^3$ represents a lower alkyl group; $R^4$ represents a hydrogen atom, hydroxymethyl group; or a mycinosyloxymethyl group; $R^5$ represents a methyl group or a methoxy group; $R^6$ represents a hydrogen atom or a methyl group; ∽ represents a single bond or a double bond; --- represents a single bond, a double bond, or an oxiran-2,3-diyl group; and —·—·—·— means that the macrolactone ring forms a 16-membered ring or a 17-membered ring.

2. A macrolide compound represented by the formula

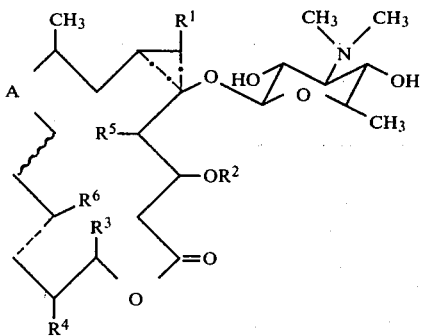

wherein A,$R^1$,$R^2$,$R^3$,$R^4$,$R^5$ and $R^6$ are same as in claim 1.

3. A compound according to claim 1 which is demycarosyl carbomycin B ethylene acetal.

4. A compound according to claim 1 which is demycarosyl-9-propionyljosamycin ethyleneacetal.

5. A compound according to claim 1 which is demycarosylspiramycin I ethylene acetal.

6. A compound according to claim 1 which is 3-acetoxy-5-hydroxy-6-(1,3-dioxalan-2-yl)methyl-4-methoxy-8-methyl-9-oxo-10, 12-hexadecadien-15-olide.

7. A compound according to claim 1 which is acetylated 3-acetoxy-5-hydroxy-6-(1,3-dioxalan-2-yl)methyl-4-methoxy-8-methyl-9-oxo-10,12-hexadecadien-15-olide.

8. A compound according to claim 2 which is the N-oxide of 3-acetoxy-5-[3,6-dideoxy-3-dimethylamino-β-D-glucopyranosyloxy]-6-(1,3-dioxolan-2-yl)methyl-4-methoxy-8-methyl-9-oxo-10,12-hexadecadien-15-olide.

9. A compound according to claim 1 which is acetylated 3-acetoxy-5-hydroxy-6-(1,3-dioxalan-2-yl)methyl-4-methoxy-8-methyl-9-oxo-10,12-hexadecadien-15-olide.

10. A compound according to claim 2 which is 3-acetoxy-5-[2,4-O-diacetyl-1,3,6-trideoxy-3-dimethylamino-β-D-glucopyranosyloxy]-6-[1,3-dioxolan-2-yl]methyl-4-methoxy-8-methyl-9-oxo-10,12-hexadecadien-15-olide.

11. A compound according to claim 2 which is 5-(3,6-dideoxy-3-dimethylamino-β-D-glucopyranosyloxy)-6-(1,3-dioxolan-2-yl)methyl-3-hydroxy-14-hydroxymethyl-4,8,12-trimethyl-9-oxo-10,12-heptadecadien-15-olide.

12. A compound according to claim 1 which is 6-(1,3-dioxolan-2-yl)methyl-3,5-dihydroxy-14-hydroxymethyl-4,8,12-trimethyl-9-oxo-10,12-heptadecadien-15-olide.

13. A compound according to claim 2 which is 5-(3,6-dideoxy-3-dimethylamino-β-D-glucopyranosyloxy)-6-formylmethyl-3-hydroxy-14-hydroxymethyl-4,8,12-trimethyl-9-oxo-10,12-heptadecadien-15-olide.

14. A compound according to claim 2 which is 5-(3,6-dideoxy-3-dimethylamino-β-D-glucopyranosyloxy)-6-(1,3-dioxolan-2- yl)-methyl-3-hydroxy-14-hydroxymethyl-4,8,12-trimethyl-9-oxo-10,12-heptadecadien-15-olide.

15. A compound according to claim 2 which is the N-oxide of 3-acetoxy-5-(3,6-dideoxy-3-dimethylamino-D-glucopyranosyloxy)-9-hydroxy-4-methoxy-8-methyl-6-(4-methyl-1,3-dioxolan-2-yl)methyl-15-hexadecanolide.

16. A compound according to claim 1 which is 3-acetoxy-5,9-dihydroxy-4-methoxy-8-methyl-6-(4-methyl-1,3-dioxolan-2-yl) methyl-15-hexadecanolide.

17. A compound according to claim 2 which is 3-acetoxy-5-(3,6-dideoxy-3-dimethylamino-β-D-glucopyranosyloxy)-9-hydroxy-4-methoxy-8-methyl-6-(4-methyl-1,3-dioxolan-2-yl)methyl-15-hexadecanolide.

18. A compound according to claim 2 which is 3-acetoxy-5-[3,6-dideoxy-4-O-(2,6-dideoxy-2-bromo-4-O-isovaleryl-3-C-methyl-α-L-altropyranosyl)-3-dimethylamino-β-D-glucopyranosyloxy]-6-(1,3-dioxolan-2-yl)-methyl-4-methoxy-8-methyl-9-oxo-10,12-hexadecadien-15-olide.

19. A compound according to claim 2 which is 3-acetoxy-5-]3,6-dideoxy-4-O-(2,6-dideoxy-2-bromo-4-O-isovaleryl-3-C-methyl-α-L-altropyranosyl)-3-dimethylamino-β-D-glucopyranosyloxy]-6-formylmethyl-4-methoxy-8-methyl-9-oxo-10,12-hexadecadien-15-olide.

20. A compound according to claim 2 which is 3-acetoxy-5-]3,6-dideoxy-4-O-(2,6-dideoxy-2-bromo-4-O-isovaleryl-3-O-methyl-3-C-methyl-α-L-altropyranosyl)-3-dimethylamino-62-D-glucopyranosyloxy]-6-(1,3-dioxolan-2-yl)methyl-4-methoxy-8-methyl-9-oxo-10,12-hexadecadien-15-olide.

21. A compound according to claim 2 which is 3-acetoxy-5-[3,6-dideoxy-4-O-(2,6-dideoxy 2-bromo-O-isovaleryl-O-methyl-3-C-methyl-α-L-altropyranosyl)-3-dimethylamino-β-D-glucopyranosyloxy]-6-formylmethyl-4-methoxy-8-methyl-9-oxo-10,12-hexadecadien-15-olide.

* * * * *